US012667478B2

(12) United States Patent
Vella

(10) Patent No.: US 12,667,478 B2
(45) Date of Patent: Jun. 30, 2026

(54) STOMA IMPLANT ASSEMBLY

(71) Applicant: John Vella, Varsity Lakes (AU)

(72) Inventor: John Vella, Varsity Lakes (AU)

( * ) Notice: Subject to any disclaimer, the term of this patent is extended or adjusted under 35 U.S.C. 154(b) by 265 days.

(21) Appl. No.: 18/277,414

(22) PCT Filed: Feb. 17, 2022

(86) PCT No.: PCT/AU2022/050106
§ 371 (c)(1),
(2) Date: Aug. 16, 2023

(87) PCT Pub. No.: WO2022/174288
PCT Pub. Date: Aug. 25, 2022

(65) Prior Publication Data
US 2024/0122739 A1    Apr. 18, 2024

(30) Foreign Application Priority Data

Feb. 17, 2021    (AU) ................................ 2021900398

(51) Int. Cl.
| | |
|---|---|
| *A61F 5/448* | (2006.01) |
| *A61F 5/44* | (2006.01) |
| *A61F 5/445* | (2006.01) |
| *A61M 39/02* | (2006.01) |

(52) U.S. Cl.
CPC ............ *A61F 5/448* (2013.01); *A61F 5/4405* (2013.01); *A61F 2005/4455* (2013.01); *A61M 39/0247* (2013.01); *A61M 2039/0261* (2013.01)

(58) Field of Classification Search
CPC ....... A61M 39/0247; A61M 2039/0261; A61F 4/445; A61F 2005/4455
See application file for complete search history.

(56) References Cited

U.S. PATENT DOCUMENTS

| | | | | | |
|---|---|---|---|---|---|
| 3,663,965 | A | * | 5/1972 | Lee, Jr. ............. | A61M 39/0247 623/23.64 |
| 4,119,100 | A | * | 10/1978 | Rickett ................... | A61F 5/445 138/93 |
| 4,183,357 | A | * | 1/1980 | Bentley ............. | A61M 39/0247 604/339 |
| 4,217,664 | A | * | 8/1980 | Faso ..................... | A61F 2/0063 600/32 |

(Continued)

FOREIGN PATENT DOCUMENTS

| | | | | | |
|---|---|---|---|---|---|
| EP | 1632201 A1 | * | 3/2006 | ............. | A61F 5/445 |
| EP | 2364678 A1 | | 9/2011 | | |

(Continued)

OTHER PUBLICATIONS

Extended European Search Report and Opinion for European Patent Application No. 22755397.1 dated Mar. 20, 2025.

*Primary Examiner* — Guy K Townsend
(74) *Attorney, Agent, or Firm* — Hoffmann & Baron, LLP

(57) ABSTRACT

The present invention relates to a stoma implant assembly comprising a base having an aperture adapted to engage an outlet. The base is adapted to engage a body of a subject and the outlet comprises a bore therethrough. The outlet comprises a distal end having a connecting portion adapted to releasably secure a second connecting portion. The present stoma plant assembly alleviates some of the disadvantages associated with presently available stoma plant assemblies.

14 Claims, 8 Drawing Sheets

(56)                References Cited

U.S. PATENT DOCUMENTS

| | | | | |
|---|---|---|---|---|
| 4,534,761 | A * | 8/1985 | Raible | A61F 5/445 128/DIG. 25 |
| 5,098,397 | A * | 3/1992 | Svensson | A61M 39/0247 604/174 |
| 5,234,408 | A * | 8/1993 | Griffith | A61M 39/0247 600/30 |
| 5,269,774 | A * | 12/1993 | Gray | A61F 5/449 604/338 |
| 5,290,251 | A * | 3/1994 | Griffith | A61F 5/445 128/898 |
| 5,423,761 | A * | 6/1995 | Hein | A61B 1/313 604/247 |
| 5,425,761 | A * | 6/1995 | Lundgren | A61M 39/0247 606/155 |
| 5,882,341 | A * | 3/1999 | Bousquet | A61M 39/0247 128/DIG. 26 |
| 6,017,355 | A * | 1/2000 | Hessel | A61F 5/445 606/186 |
| 6,438,397 | B1 * | 8/2002 | Bosquet | A61B 5/14532 600/344 |
| 6,726,660 | B2 * | 4/2004 | Hessel | A61F 5/445 604/338 |
| 7,699,824 | B2 * | 4/2010 | Axelsson | A61F 5/4407 604/326 |
| 7,935,096 | B2 * | 5/2011 | Johansson | A61M 25/02 604/338 |
| 8,647,304 | B2 * | 2/2014 | Axelsson | A61F 5/445 604/164.04 |
| 8,821,462 | B2 * | 9/2014 | Axelsson | A61F 5/445 604/332 |
| 8,852,217 | B2 * | 10/2014 | Woodruff | A61F 5/0056 606/151 |
| 8,998,862 | B2 * | 4/2015 | Hanuka | A61F 5/4405 604/318 |
| 9,226,848 | B2 * | 1/2016 | Johansson | A61F 5/445 |
| 9,615,961 | B2 * | 4/2017 | Johansson | A61F 5/445 |
| 10,265,211 | B2 * | 4/2019 | Brönnimann | A61F 5/449 |
| 10,285,848 | B2 * | 5/2019 | Brönnimann | A61F 5/445 |
| 11,607,335 | B2 * | 3/2023 | Brönnimann | A61F 5/445 |
| 2001/0051794 | A1 * | 12/2001 | Bestetti | A61M 39/0247 604/95.05 |
| 2002/0099344 | A1 * | 7/2002 | Hessel | A61F 5/445 604/338 |
| 2004/0006396 | A1 * | 1/2004 | Ricci | B23K 26/355 623/32 |
| 2004/0184876 | A1 * | 9/2004 | Hessel | A61F 5/448 403/326 |
| 2006/0052759 | A1 * | 3/2006 | Johansson | A61M 25/02 604/277 |
| 2007/0244452 | A1 * | 10/2007 | Axelsson | A61F 5/448 604/338 |
| 2009/0192464 | A1 * | 7/2009 | Axelsson | A61M 39/0247 604/164.04 |
| 2010/0174255 | A1 * | 7/2010 | Axelsson | A61F 5/448 604/338 |
| 2011/0178540 | A1 * | 7/2011 | Axelsson | A61F 5/445 606/153 |
| 2011/0196324 | A1 * | 8/2011 | Johansson | A61M 25/02 604/338 |
| 2011/0251452 | A1 * | 10/2011 | Villani | A61F 5/445 600/37 |
| 2012/0123361 | A1 * | 5/2012 | Johansson | A61F 5/445 604/338 |
| 2012/0289916 | A1 * | 11/2012 | Johansson | A61M 25/02 604/338 |
| 2014/0052085 | A1 * | 2/2014 | Johansson | A61F 5/445 604/338 |
| 2016/0030227 | A1 * | 2/2016 | Brönnimann | A61F 5/445 604/338 |
| 2016/0045358 | A1 * | 2/2016 | Brönnimann | A61F 5/449 604/338 |
| 2016/0045359 | A1 * | 2/2016 | Brönnimann | A61F 5/449 604/338 |
| 2019/0216631 | A1 | 7/2019 | Brönnimann et al. | |
| 2024/0374791 | A1 * | 11/2024 | Kjellin | A61L 31/127 |

FOREIGN PATENT DOCUMENTS

| | | | | |
|---|---|---|---|---|
| EP | 3517079 | A1 | 7/2019 | |
| GB | 2511825 | A * | 9/2014 | A61F 5/445 |
| JP | H4-189351 | A | 7/1992 | |
| WO | 2012/007755 | A2 | 1/2012 | |
| WO | 2017/216302 | A2 | 12/2017 | |
| WO | WO-2019197291 | A1 * | 10/2019 | A61F 5/449 |

* cited by examiner

STOMA IMPLANT ASSEMBLY

CROSS-REFERENCE TO RELATED APPLICATIONS

The present application is a national phase entry under 35 USC § 371 of International Application PCT/AU2022/050106, filed Feb. 17, 2022, which claims the benefit of and priority to Australian Patent Application No. 2021900398, filed Feb. 17, 2021. The entire disclosures of the above applications are incorporated herein by reference.

FIELD OF THE INVENTION

The present invention relates to the field of medical devices. More particularly, the invention relates to a stoma implant assembly and method of using the stoma implant assembly.

BACKGROUND TO THE INVENTION

Any reference to background art herein is not to be construed as an admission that such art constitutes common general knowledge in Australia or elsewhere.

Infection of the abdomen, injury of the colon or rectum, or partial or complete blockages of the bowel can cause significant health complications to a person. In this regard, a colostomy may be required as either a temporary or permanent solution.

Colostomy is a surgical procedure that conveys one end of the large intestines through the abdominal wall. In this regard, the colon is diverted through an incision in the abdominal wall to create a stoma. A stoma is the term used to describe an opening where a vessel (such as a stoma bag) can be utilized for collecting bodily fluids, such as feces and urine.

Typically, a stoma bag is attached to the skin of a patient by adhesive tape. However, attachment in this manner is prone to leakage, severe skin irritations and infections that can lead to discomfort and reduced quality of life.

It would be advantageous to address one or more of the issues mentioned hereinabove, or to provide a commercial alternative to the consumer.

SUMMARY OF THE INVENTION

In a first aspect, although it need not be the only or indeed the broadest aspect, the invention resides in a stoma implant assembly comprising:

a base having an aperture adapted to engage an outlet, wherein the base is adapted to engage a body of a subject;

wherein the outlet comprises a distal end having a connecting portion adapted to releasably secure a second connecting portion, and wherein the outlet comprises a bore therethrough.

In certain embodiments, the base comprises one or more engagement apertures. In some embodiments, the one or more engagement apertures are located concentrically around the aperture.

In a preferred embodiment, the base is an annular base.

In an embodiment, the outlet and base form an interference fit arrangement. In one embodiment, the outlet and base form a substantially fluid tight seal. In an embodiment, the outlet and base form a fluid tight seal.

In one embodiment, the stoma implant assembly further comprises a cap and/or a stoma bag comprising the second connecting portion. The second connecting portion is reciprocal or complementary to the connecting portion. A seal is suitably formed between the second connecting portion and the first connecting portion, and between any member(s) therebetween.

In certain embodiments, the bore extends centrally along a longitudinal axis of the outlet. In a preferred embodiment, in use, the bore is perpendicular to the base. In one embodiment, the bore of the outlet has a diameter between about 5 mm and about 50 mm, between about 10 mm and about 40 mm, between about 11 mm and about 39 mm, between about 10 mm and about 15 mm, between about 16 mm and about 35 mm, between about 30 mm and about 40 mm, about 11 mm or about 39 mm.

Preferably, the outlet comprises a spacing between a portion that forms an interference fit with the base and the connecting portion. Preferably, spacing is at least about 3 mm, at least about 5 mm, between about 3 mm and about 10 mm, or about 5 mm in length.

In one embodiment, connecting portion is located at or adjacent the distal end of the outlet. In an embodiment, the connecting portion is located adjacent the distal end of the outlet. In some embodiments, the connecting portion is located at the distal end of the outlet. In certain embodiments, the connecting portion comprises a flange or extension about the outlet. The extension or flange extends away from the outlet.

In certain embodiments, the connecting portion comprises a pair of spaced apart protrusions. In one embodiment, the pair of spaced apart protrusions form a curved channel therebetween. In some embodiments, the spaced apart protrusions are adapted to receive a clip.

In one embodiment, the stoma implant assembly further comprises a clip. In an embodiment, the clip is an adjustable clip. In embodiments, the clip is a biased clip. In embodiments, the clip is operable between an open configuration and a closed configuration. In an embodiment, the clip is biased towards the closed configuration.

In an embodiment, the clip comprises an elongate member having a first end and a second end. In an embodiment, the elongate member forms a loop. In a further embodiment, the second end extends beyond the first end and forms an acute angle to abut the loop.

In an embodiment, the connecting portion comprises a male thread. In an embodiment, the male thread is located at, or adjacent, a distal end of the outlet.

In embodiments, the stoma implant assembly further comprises a cover. In some embodiments, the cover comprises the second connecting portion. In an embodiment, the second connecting portion comprises a female thread. The female thread is reciprocal to the male thread.

In one embodiment, the cover comprises a seal member adapted to form a seal between the cover and the outlet. In one embodiment, the seal member is in the form of an O-ring.

In some embodiments, the cover comprises a check valve. In embodiments, the cover is adapted to connect to, or is formed with, a stoma bag. In embodiments, the check valve is a ball check valve or diaphragm check valve.

In one embodiment, the base, outlet and/or cover is formed of a biocompatible material. In one embodiment, the material is suitably a polymer. In an embodiment, the material is a semi-crystalline thermoplastic. In embodiments, the material is a polyetheretherketone. In a preferred embodiment, the material is PEEK Polyetheretherketone.

In an embodiment, the stoma implant assembly for use in colostomy. In further embodiments, the stoma implant assembly when used in colostomy.

In a second aspect, the invention resides in a method for fitting a stoma implant assembly in a subject, the method including the steps of:

aligning an aperture of a base under the skin with an incision in the abdomen of the subject, wherein the aperture is adapted to engage an outlet; and securing the outlet with the base through the incision, wherein the outlet comprises a distal end having a connecting portion adapted to releasably secure a second connecting portion, wherein the outlet comprises a bore therethrough, to thereby fitting the stoma implant assembly in a subject.

The stoma implant assembly and components thereof may be as substantially described hereinabove for the first aspect.

In one embodiment, the method further includes the step of locating a stoma of the subject through the bore.

In an embodiment, the method further includes the step of locating a stoma bag or cap comprising the second connecting portion over the connecting portion. In a further embodiment, the method further includes the step of engaging the clip over the second connecting portion and the connecting portion.

In embodiments, the method further includes the step of disengaging the clip over second connecting portion. In this regard, there may be a further step of placing another stoma bag or cap over the connecting portion and locating the clip thereover.

In one embodiment, the method further includes the step of locating a cover comprising the second connecting portion over the connecting portion of the outlet.

In embodiments, the method further includes the step of connecting a stoma bag to a stoma bag connecting portion of the cover.

The various features and embodiments of the present invention referred to in the individual sections above and in the description which follows apply, as appropriate, to other sections, mutatis mutandis. Consequently features specified in one section may be combined with features specified in other sections as appropriate.

Further features and advantages of the present invention will become apparent from the following detailed description.

BRIEF DESCRIPTION OF THE DRAWINGS

To assist in understanding the invention and to enable a person skilled in the art to put the invention into practical effect, embodiments of the invention will be described by way of example only with reference to the accompanying drawings, in which.

DETAILED DESCRIPTION OF THE INVENTION

Figure 1:
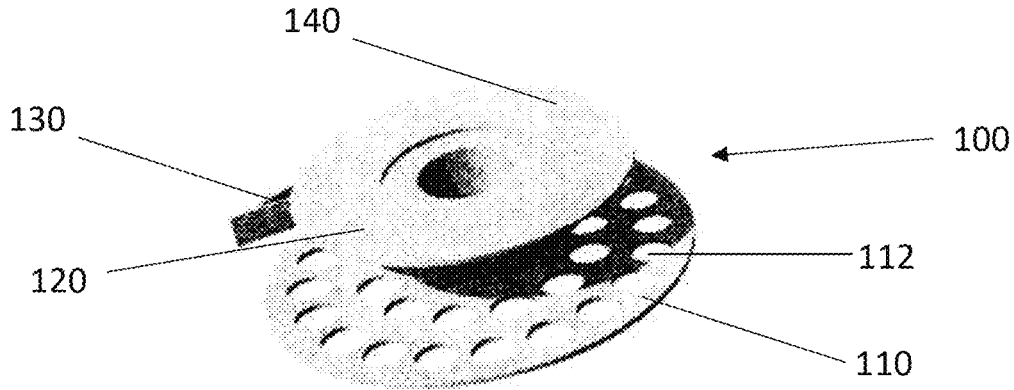
FIG. 1 shows an embodiment of the stoma implant assembly of the present invention.

Embodiments of the present invention reside primarily in a stoma implant assembly. Accordingly, the assembly and method steps have been illustrated in concise schematic form in the drawings, showing only those specific details that are necessary for understanding the embodiments of the present invention so as to not obscure the disclosure with excessive detail that will be readily apparent to those of ordinary skill in the art having the benefit of the present description.

In this specification, adjectives such as first and second, left and right, and the like may be used solely to distinguish one element or action from another element or action without necessarily requiring or implying any actual such relationship or order.

Words such as "comprises" or "includes" are intended to define a non-exclusive inclusion, such that a process, method, article, or apparatus that comprises a list of elements does not include only those elements but may include other elements not expressly listed, including elements that are inherent to such a process, method, article, or apparatus.

As used herein, the term 'about' means the amount is nominally the number following the term 'about' but the actual amount may vary from this precise number to an unimportant degree.

As used herein, the term 'stoma bag' refers to a waterproof pouch utilized to collect fluids from the body via. a stoma. A 'stoma bag' is also known as a colostomy bag or ostomy bag.

As used herein, the term 'stoma' refers to an opening in the abdomen where a vessel can be utilized for collecting fluids from the body.

It will be appreciated that the dimensions provided in the figures are for exemplification purposes only.

The present invention is predicated on the finding that an improved stoma implant assembly can be utilized to collect waste and/or other fluids from the body. The present invention allows a stoma bag to collect fluids from the body of a subject whilst alleviating the issue of skin irritations, infections, discomfort and/or leakage.

Figure 2:
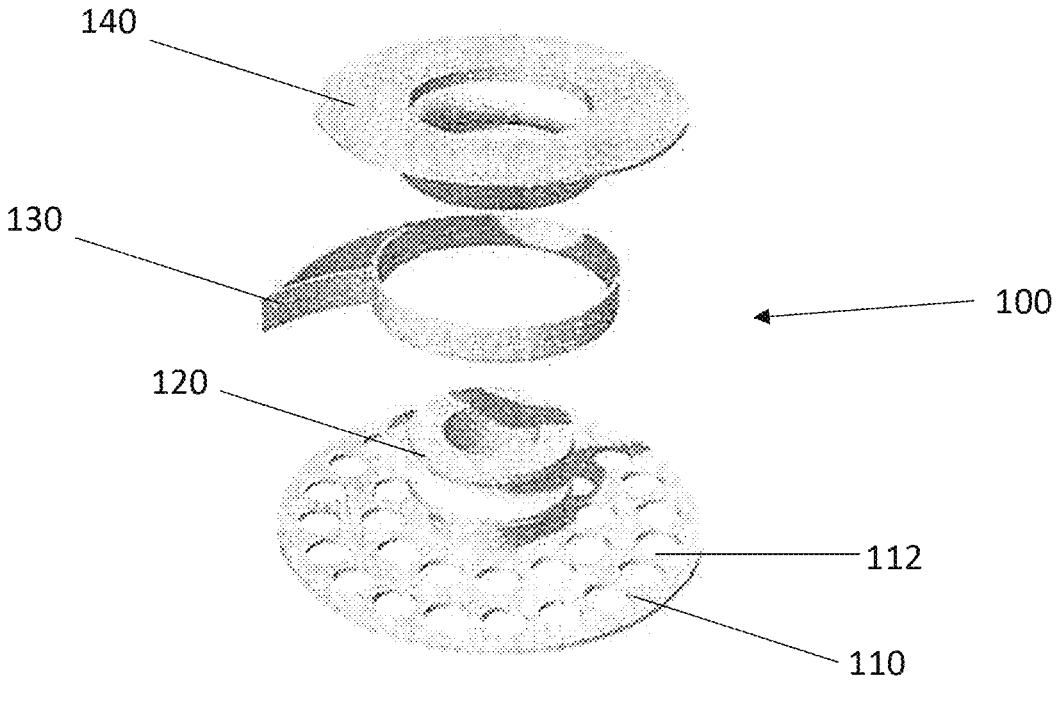
FIG. 2 shows an exploded view of the stoma implant assembly of FIG. 1.

Shown in FIG. 1 is an embodiment of a stoma implant assembly of the present invention. FIG. 2 shows an exploded version of the stoma implant assembly of FIG. 1. Stoma implant assembly 100 comprises a base 110 having an aperture (not shown) and an outlet 120. The base 110 is adapted to engage the outlet 120. Furthermore, the base 110 is adapted to engage the body of a subject under the skin such that the base 110 is below the skin and the outlet 120 passes through an incision in the abdomen of the subject.

In the embodiment shown in FIG. 1, the stoma implant assembly 100 may further comprises a clip 130. In one embodiment, the clip 130 is an adjustable clip. The stoma implant assembly 100 may further comprise a cap or a seal for a stoma bag. In the embodiment shown in FIG. 1, the stoma implant assembly 100 is shown with a seal 140 of a stoma bag (not shown for exemplification purposes).

Figure 3:
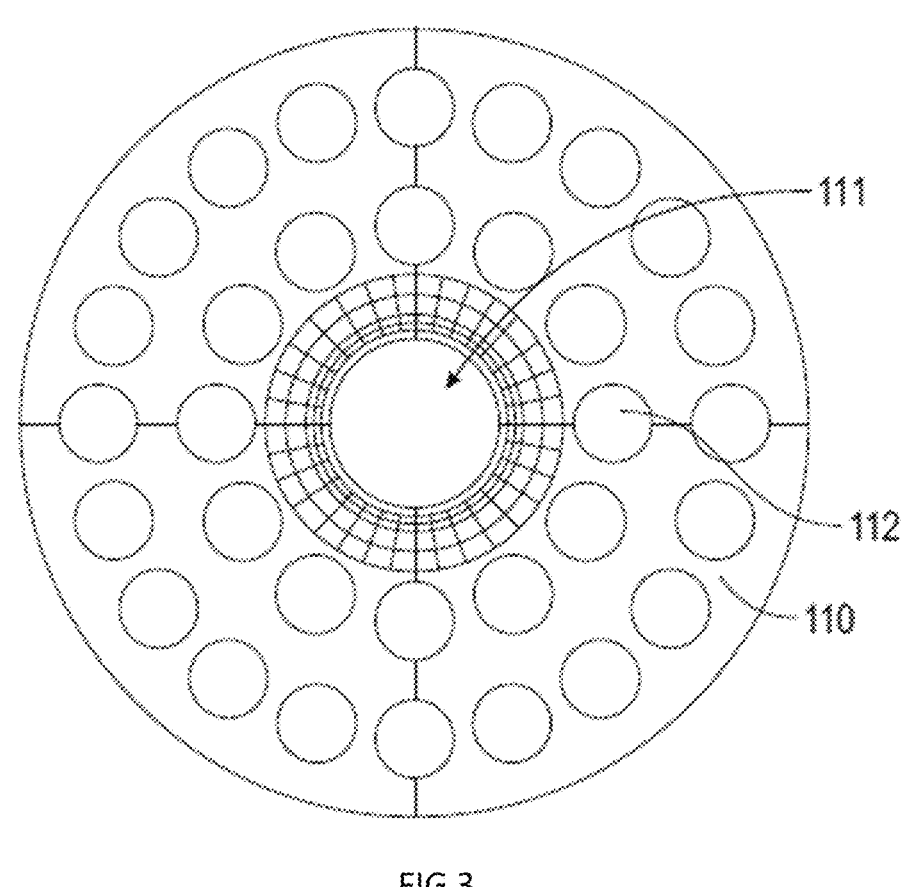
FIG. 3 shows a top view of the base.

Shown in FIG. 3 is an embodiment of the base 110. The base 110 comprises an aperture 111. In one embodiment, the aperture 111 is centrally located in the base 110. In the embodiment shown, the base 110 is in the form of an annulus. The base 110 is adapted to be placed under the skin. The aperture 111 of the base 110 is aligned with the incision and an outlet 120 may be secured to the base 110 through the incision. In one embodiment, the base 110 is dimensioned such that the outlet 120 forms an interference fit (or friction fit) arrangement therewith. The interference fit advantageously allows the outlet to be easily attached to the base. However, it will be appreciated that other forms of attachment known to the person skilled in the art may be utilized to attach the outlet 120 to the base 110. The stoma may be passed through the outlet 120 such that bodily fluids can be collected externally from the body.

The base 110 being under the skin allows the base 110 to form a barrier to leakage. In one embodiment, the base 110 comprises one or more engagement apertures 112. In some embodiments, the one or more engagement apertures are located concentrically around the aperture. It is postulated that the one or more engagement apertures 112 allows for more secure attachment to the subject and alleviates the problem of leakage.

In one embodiment, the base 110 is formed of a material that is biocompatible with the human body. In one embodiment, the base 110 is formed of titanium. In one embodiment, the material is suitably a polymer. In an embodiment, the material is a semi-crystalline thermoplastic. In embodiments, the material is a polyetheretherketone. In a preferred embodiment, the material is PEEK Polyetheretherketone. One source of PEEK Polyetheretherketone is provided under the trade name SustaPEEK MG (Medical Grade) PEEK manufactured by Rochling.

Figure 4:
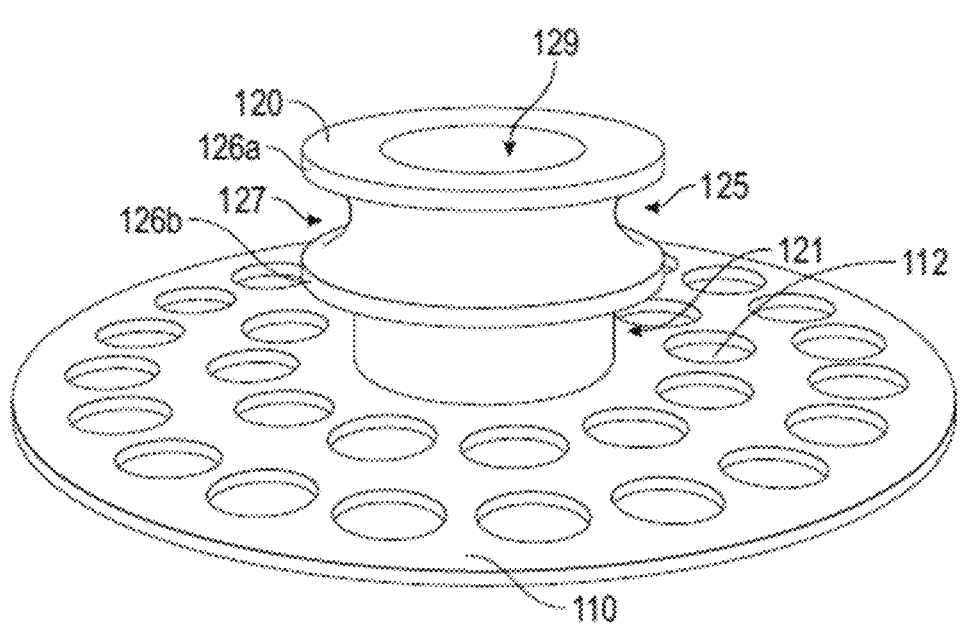
FIG. 4 shows an embodiment of the base secured to the outlet.
Figure 5:
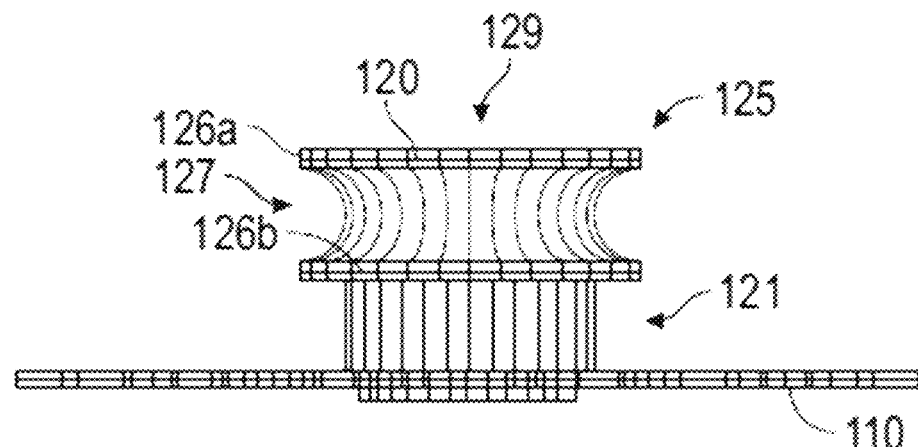
FIG. 5 shows a side view schematic of the base and outlet

Shown in FIG. 4 is an embodiment of the base 110 forming an interference fit with outlet 120. Shown in FIG. 5 is a side view of the embodiment shown in FIG. 4. The outlet 120 comprises a proximal end (in interference engagement with the base 110) and a distal end. The proximal end is dimensioned to form the interference arrangement with the base 110. The distal end of the outlet 120 comprises a connecting portion 125. The connecting portion 125 is adapted to engage a cap, stoma seal or cover (mentioned in more detail hereinafter).

The outlet 120 comprises a bore 129 therethrough. The bore 129 extends through a longitudinal axis of the outlet 120. The bore 129 is centrally located in the outlet 120. The bore 129 is preferably substantially perpendicular to a surface of the base 110, in use. A stoma is suitably passed through the bore 129 in outlet 120.

In the embodiment shown, the connecting portion 125 comprises a pair of spaced apart protrusions 126*a*, 126*b* extending radially outwardly. The spaced apart protrusion 126*a* and 126*b* form a channel 127 extending around the distal end of the outlet 120. The channel 127, as shown in FIG. 4, may be in the form of a concave channel. It is postulated that this advantageously provides a smooth surface to form a watertight seal.

In another embodiment, the connecting portion may suitably comprise an outer threaded surface. In this regard, the connecting portion may suitably comprise a male threaded portion adapted to be received by a female threaded portion. The connecting port Preferably, the outlet 120 comprises a spacing 121 between the portion that forms an interference fit with the base 110 and the connecting portion 125. Preferably, spacing 121 is at least about 3 mm, at least about 5 mm, between about 3 mm and about 10 mm, or about 5 mm. This advantageously allows the connecting portion 125, in use, to be spaced from the peristomal skin of the subject. This advantageously allows for a stoma bag fastened or secured to the connecting portion 125 to be spaced apart from the skin. This advantageously alleviates the problem of skin irritations, infections and/or discomfort. Furthermore, this alleviates the requirement to utilize adhesive to adhere a stoma bag to the patient.

In one embodiment, the outlet 120 is formed of a biocompatible material or a composite material. In one embodiment, the outlet 120 is formed of titanium or polyurethane. In one embodiment, the material is suitably a polymer. In an embodiment, the material is a semi-crystalline thermoplastic. In embodiments, the material is a polyetheretherketone. In a preferred embodiment, the material is PEEK Polyetheretherketone. One source of PEEK Polyetheretherketone is provided under the trade name SustaPEEK MG (Medical Grade) PEEK manufactured by Rochling.

Figure 6:
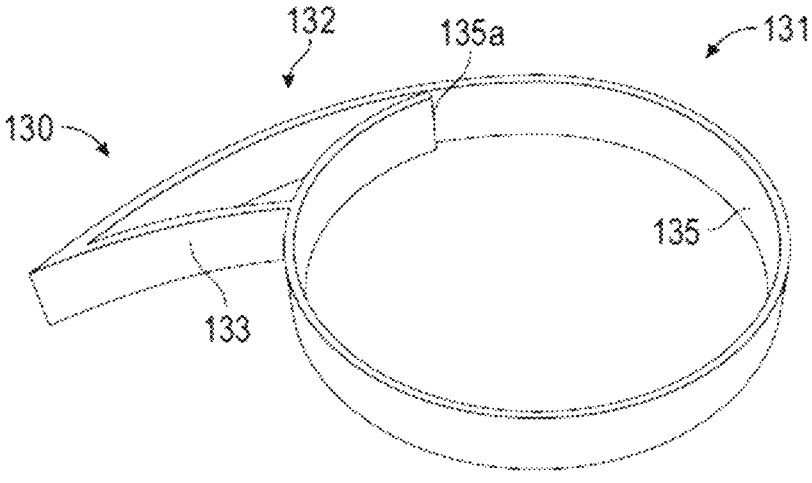
FIG. 6 shows an embodiment of the clip.

Shown in FIG. 6 is an embodiment of clip 130 adapted to engage the connecting portion 125. As previously mentioned, the clip 130 is an adjustable clip. In the embodiment shown in FIG. 6, the clip 130 is biased. In this regard, the clip 130 can be utilized to secure to the connecting portion 125. The clip 130 and the connecting portion 125 (and any member therebetween) form a seal therebetween. Preferably, the seal formed is substantially watertight.

The clip 130 comprises elongate member 135. The elongate member 135 comprises a first end 135*a* and a second end 135*b*. The elongate member is shaped such that it forms a loop 131. As shown, the loop 131 of the elongate member 135 does not connect with a first end 135*a* of elongate member 135; rather, the second end 135*b* extends beyond the first end 135*a* thereof (shown by arrow 132), and forms an acute angle to abut portion of the elongate member 135 adjacent the first end 135*a*. As shown, the elongate member 125 abuts the loop 131. This shaping allows the diameter of the loop 131 to be easily adjusted. In this regard, the acute angle could be reduced by applying pressure to section 133 such that the second end 135*b* does not engage the loop 131 and this allows the loop 131 to enlarge in diameter and fit over one of the two protrusions of the connecting portion 125 and over the channel 127. In one embodiment, the clip is a biased clip. As pressure is released, section 133 engages the loop 131 and reduces the diameter thereof. This allows the clip 130 to engage the connecting portion 125 and form a seal therebetween. It will be appreciated that the clip 130 is operatable between an open configuration (when pressure is applied to section 133 and the diameter of the substantially circular portion 131 is enlarged) and a closed configuration (when pressure is not applied to section 133 and the diameter of the loop 131 is smaller). It will be appreciated that the closed configuration will apply pressure to the connecting portion 125 and form a seal therebetween.

Figure 7:
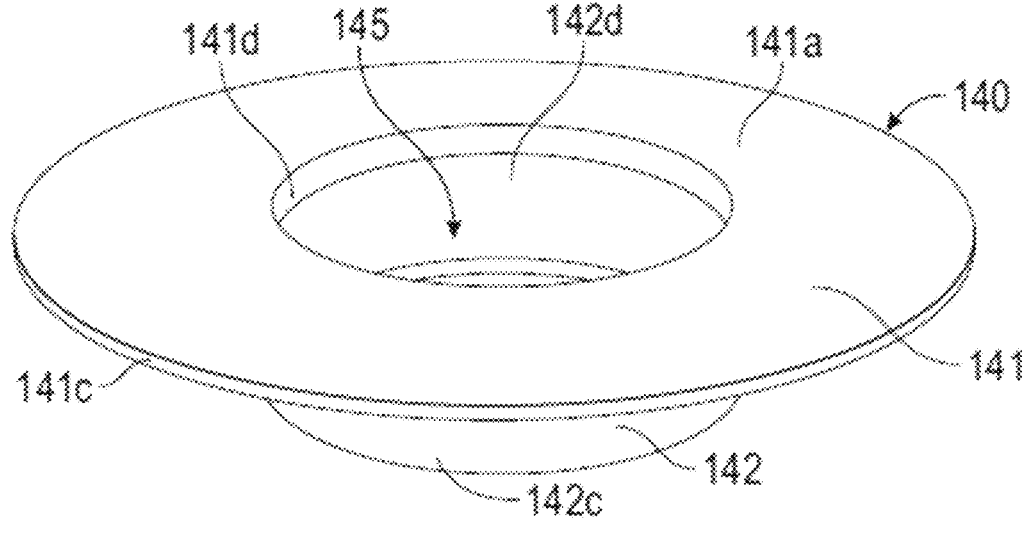
FIG. 7 shows a seal for a stoma bag.

FIG. 7 shows a seal 140 of a stoma bag. The seal 140 is adapted to be utilized with a stoma bag. The seal may be utilized with an opening in the stoma bag. For instance, the seal 140 can be utilized to seal an aperture in a stoma bag. The seal 140 can then be utilized with the clip 130 to secure the seal 140 (and thus stoma bag) to the outlet 120.

The seal 140 comprises a body 141 having an aperture 145. In one embodiment, the body 141 is in the form of an annulus. The body 141 comprises a first surface 141*a* and an opposing second surface 141*b* (not shown). The first surface 141*a* and the second opposed surface 141*b* are connected by an outer surface 141c and an inner surface 141d. The second surface 141b is provided with a cylindrical protrusion 142. The cylindrical protrusion 142 comprises an outer wall 142c and an inner wall 142d. The inner wall 142d is continuous with the inner surface 141d. The cylindrical protrusion 142 is dimensioned such that it engages the connecting portion 125. In an embodiment, the cylindrical portion is complementary to the connecting portion 125. In one embodiment, the seal 140 is formed of a resilient and deformable material so that application of the clip 130 over the cylindrical protrusion 142 causes the cylindrical protrusion to deform and form a seal with the connecting portion 125. This allows the stoma bag attached to the seal 140 to collect fluids from the body without leakage. Furthermore, the clip 130 can be easily removed and the stoma bag comprising the seal removed.

In one embodiment, the resilient and deformable material is suitably a polymer. In one embodiment, the resilient and deformable material is suitably rubber or latex. In an embodiment, the material is a semi-crystalline thermoplastic. In embodiments, the material is a polyetheretherketone. In a preferred embodiment, the material is PEEK Polyetheretherketone. One source of PEEK Polyetheretherketone is provided under the trade name SustaPEEK MG (Medical Grade) PEEK manufactured by Rochling.

In certain situations, a subject with a stoma implant assembly may wish to remove the stoma bag for a short period of time. For instance, the subject may wish to partake in activities in which a stoma bag may be an inconvenience. In these situations, a cap may be utilized to close off the stoma. The cap suitably comprises the second connecting portion that is reciprocal to the connecting portion 125. However, the second connecting portion is closed and, in use, does not expose the stoma to the external environment. Preferably, the cap forms a watertight seal with the outlet.

Figure 9:
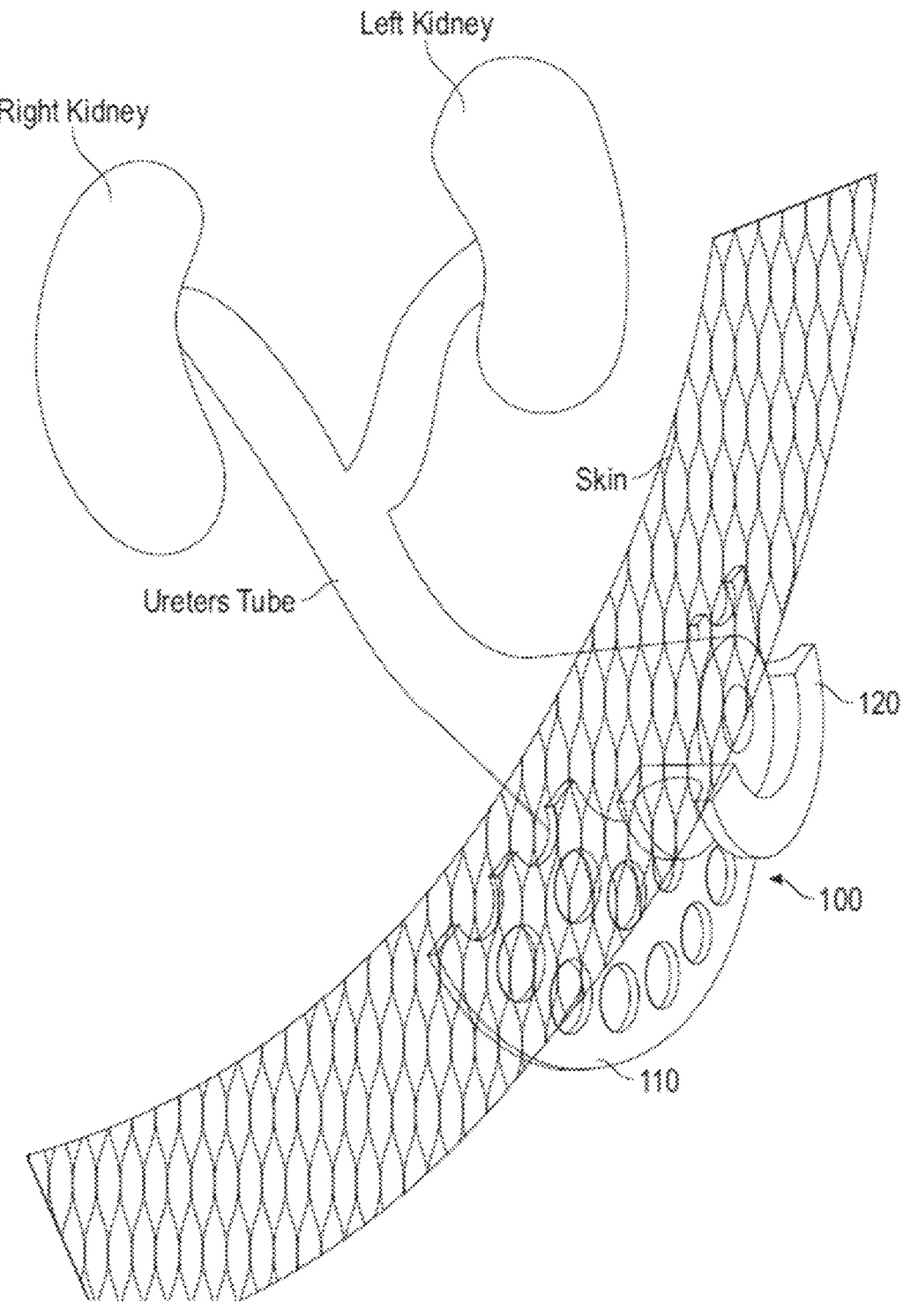
FIG. 9 shows the stoma implant assembly connected to the ureters tube.
Figure 10:
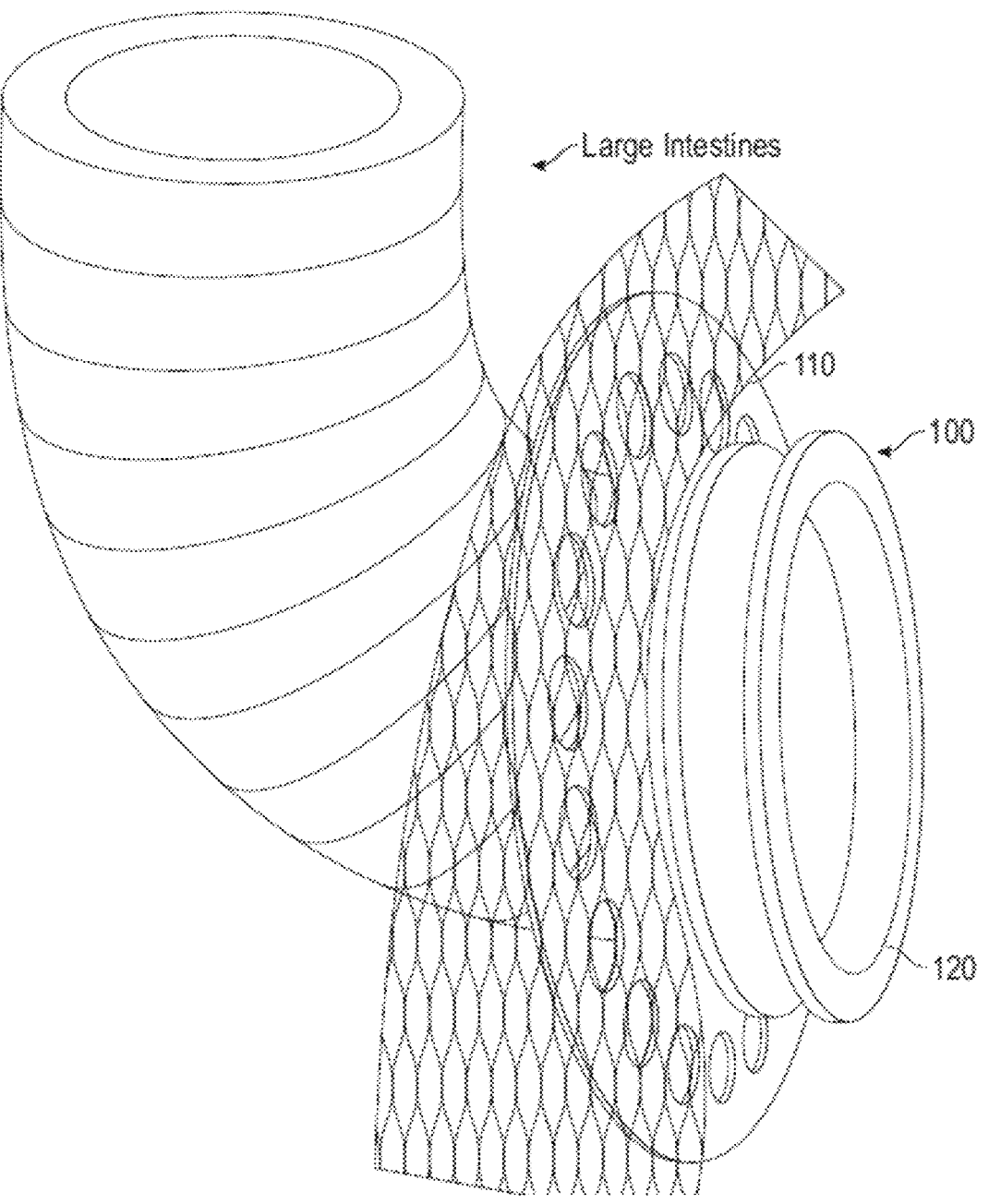
FIG. 10 shows the stoma implant assembly connected to the large intestines.

The embodiments shown in FIGS. 1 to 7 depict a stoma implant assembly utilized for connection to the ureters tube (FIG. 9). The use of a stoma implant assembly in this situation requires a smaller bore. In other situations, such as in connection to the large intestines (FIG. 10), a larger bore may be required. As shown in these figures, the base 110 of the stoma implant assembly 100 resides under the skin of the patient and the outlet 120 extends through an incision of the abdomen.

Figure 8:
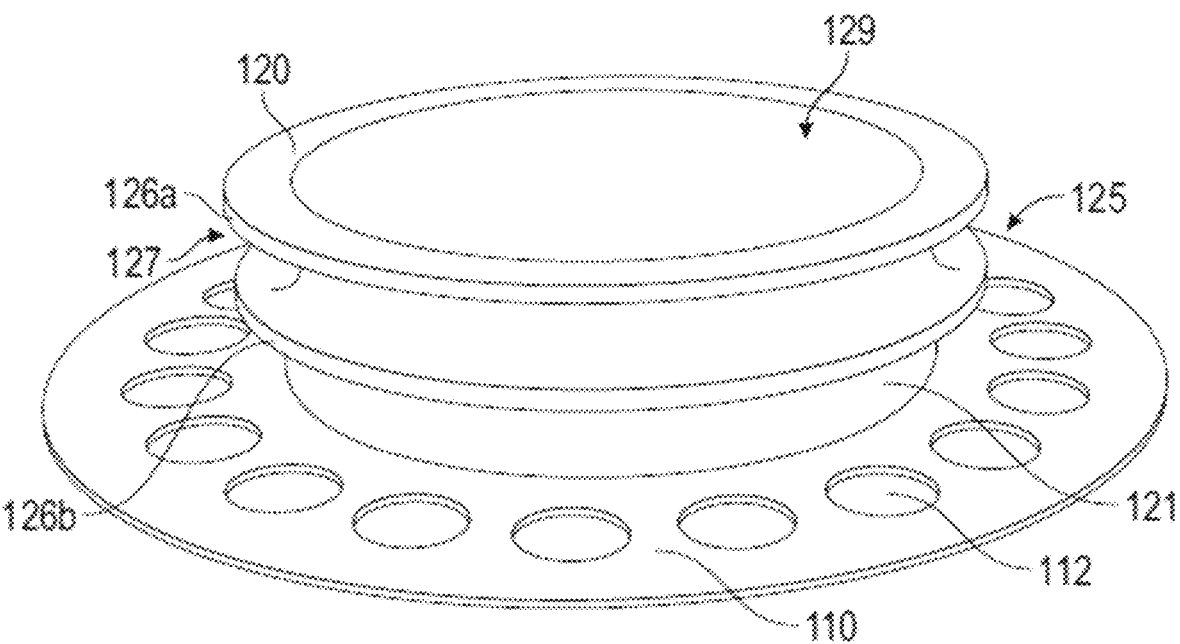
FIG. 8 shows another embodiment of the base.

Shown in FIG. 8 is another embodiment of the base and the outlet wherein the bore of the outlet and the aperture of the base is larger. For ease of description, the same numbering has been utilized as for the above as these features are substantially similar as those described hereinabove, apart from some dimensions.

In one embodiment, the bore of the outlet may have a diameter between about 5 mm and about 50 mm, between about 10 mm and about 40 mm, between about 11 mm and about 39 mm, between about 10 mm and about 15 mm, between about 16 mm and about 35 mm, between about 30 mm and about 40 mm, about 11 mm or about 39 mm.

In the embodiment where the base and outlet are cylindrical or an annulus, the diameter of the base is greater than the diameter of the outlet. This allows the base to anchor the subject under the skin.

In certain embodiments, the diameter of the base is suitably between 20 mm and about 100 mm, between about 40 mm and about 90 mm, between about 50 mm and 70 mm, between about 40 mm and about 60 mm, between about 60 mm and about 80 mm, about 50 mm or about 70 mmm.

In certain embodiments, the connecting portion (widest part of the connecting portion; the spaced apart protrusions)

has a diameter of between about 15 mm and about 60 mm, between about 19 mm and about 47 mm, between about 15 mm and about 25 mm, between about 45 mm and about 55 mm, about 19 mm, or about 47 mm.

In an embodiment the spacing has a diameter of suitably between 10 mm and about 50 mm, between 14 mm and about 42 mm, between about 10 mm and about 20 mm, between about 35 mm and about 45 mm, about 14 mm, or about 42 mm.

Figure 11:
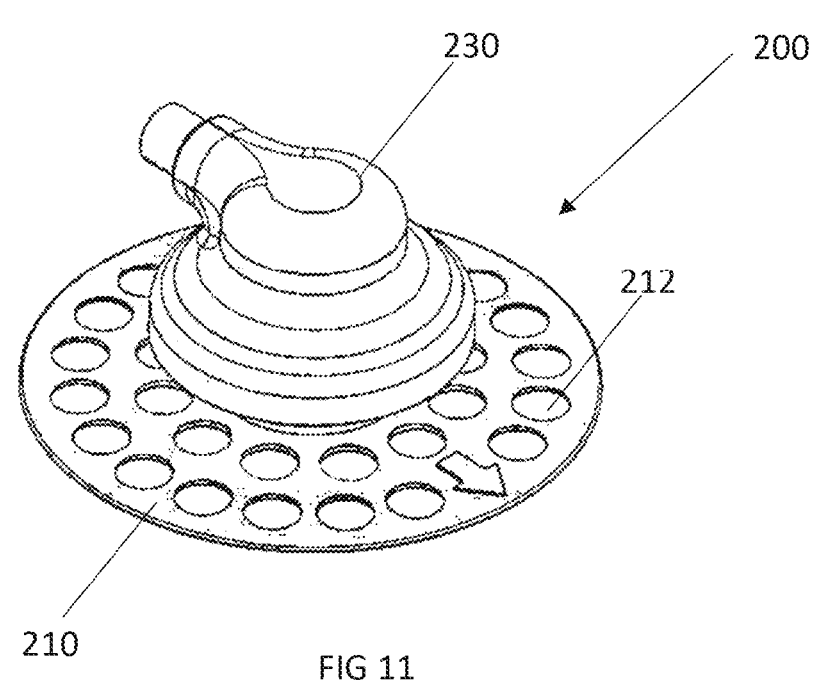
FIG. 11 shows another embodiment of the stoma implant assembly.

Shown in FIG. 11 is an embodiment of another stoma implant assembly. The stoma implant 200 suitably comprises a base 210 having an aperture 211 and an outlet 220. The base 210 is adapted to engage the outlet 220. Furthermore, the base 210 is adapted to engage the body of the subject under the skin such that the case 210 is below the skin and the outlet passes through an incision in the abdomen.

Figure 12:
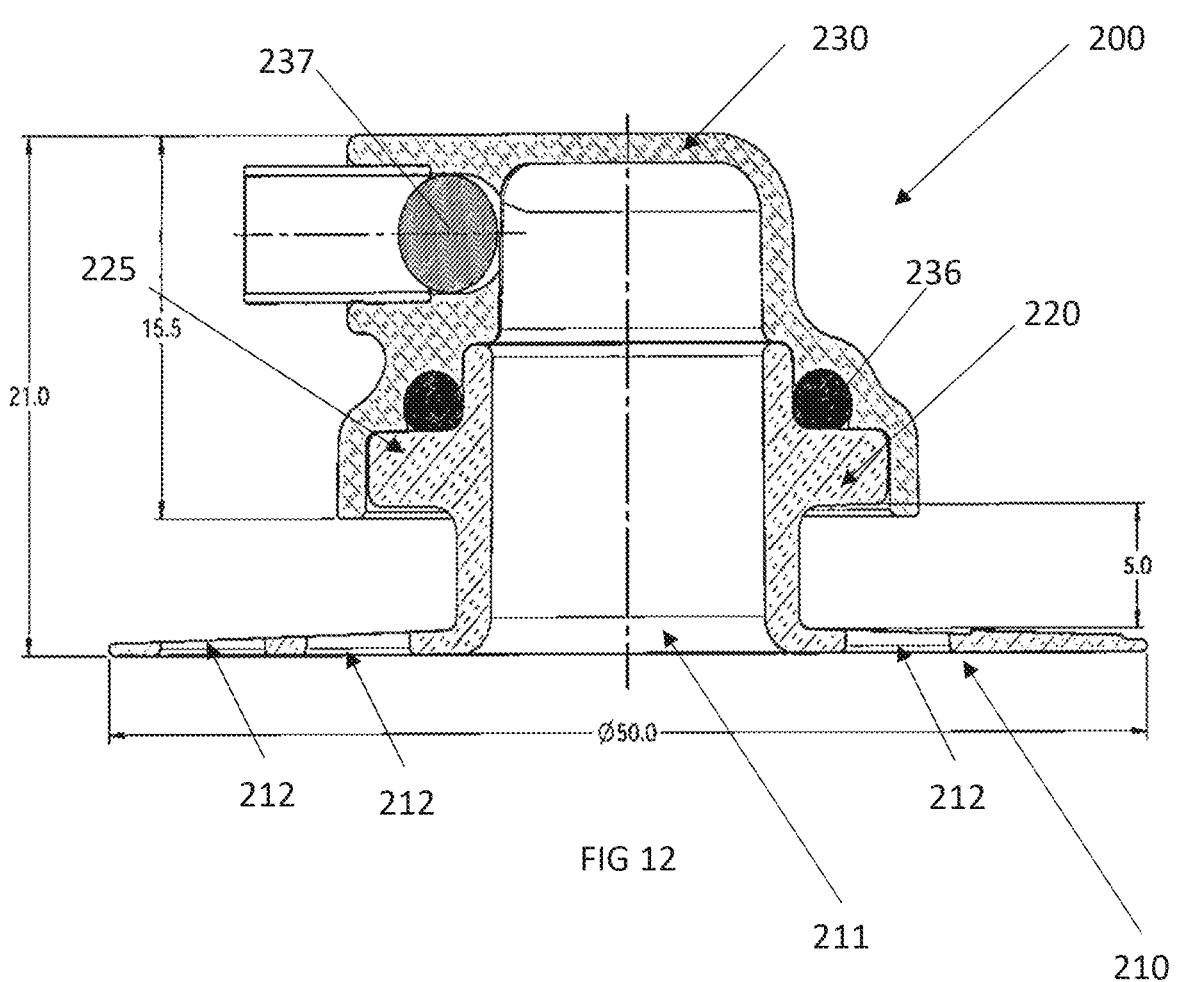
FIG. 12 shows a cross-section of the stoma implant assembly of FIG. 11.

FIG. 12 shows a cross-section of the embodiment shown in FIG. 11. As shown, similar to base 100 above, base 210 suitably comprises an aperture 211. In one embodiment, the aperture 211 is centrally located in the base 210. In the embodiment shown, the base 210 is in the form of an annulus. The base 210 is adapted to be placed under the skin. The aperture 211 of the base 210 is aligned with the incision and an outlet 220 may be secured to the base 210 through the incision. In one embodiment, the base 210 is dimensioned such that the outlet 220 forms an interference fit (or friction fit) arrangement therewith. The interference fit advantageously allows the outlet to be easily attached to the base. However, it will be appreciated that other forms of attachment known to the person skilled in the art may be utilized to attach the outlet 220 to the base 210. The stoma may be passed through the outlet 220 such that bodily fluids can be collected externally from the body. In one embodiment, the outlet 220 and the base 210 are suitably integrally formed. In another embodiment, the outlet 220 and the base are discrete components.

The base 210 being under the skin allows the base 210 to form a barrier to leakage. In one embodiment, the base 210 comprises one or more engagement apertures 212. In some embodiments, the one or more engagement apertures are located concentrically around the aperture 211. It is postulated that the one or more engagement apertures 212 allows for more secure attachment to the subject and alleviates the problem of leakage.

In one embodiment, the base 210 is formed of a material that is biocompatible with the human body. In one embodiment, the base 210 is formed of titanium. In one embodiment, the material is suitably a polymer. In an embodiment, the material is a semi-crystalline thermoplastic. In embodiments, the material is a polyetheretherketone. In a preferred embodiment, the material is PEEK Polyetheretherketone. One source of PEEK Polyetheretherketone is provided under the trade name SustaPEEK MG (Medical Grade) PEEK manufactured by Rochling.

The outlet 220 comprises a proximal end (in interference engagement with the base 210) and a distal end. The proximal end is dimensioned to form the interference arrangement with the base 210. The distal end of the outlet 220 comprises a connecting portion 225. In the embodiment shown in FIG. 11 and FIG. 12, the connecting portion forms part of a securing assembly with a cover 230 mentioned hereinafter. In the embodiment shown in FIGS. 11 and 12, the cover 230 comprises a second connecting portion 235 which form the securing assembly with the connecting portion 225. The connecting portion 225 may be in the form of a flange or extension with one or more indents and channels (not shown) which engage a respective protrusion of the second connecting portion 235. Once engaged, the protrusion can be twisted such that the cover 230 is sealed and retained with the outlet 220. The protrusions are suitably inserted into the indents and twisted into the channel to securely attached thereto.

In one embodiment, the base 110 is formed of a material that is biocompatible with the human body. In one embodiment, the base 110 is formed of titanium. In one embodiment, the material is suitably a polymer. In an embodiment, the material is a semi-crystalline thermoplastic. In embodiments, the material is a polyetheretherketone. In a preferred embodiment, the material is PEEK Polyetheretherketone. One source of PEEK Polyetheretherketone is provided under the trade name SustaPEEK MG (Medical Grade) PEEK manufactured by Rochling.

In one embodiment, the outlet 220 is formed of a material that is biocompatible with the human body. In one embodiment, the outlet 220 is formed of titanium. In one embodiment, the material is suitably a polymer. In an embodiment, the material is a semi-crystalline thermoplastic. In embodiments, the material is a polyetheretherketone. In a preferred embodiment, the material is PEEK Polyetheretherketone. One source of PEEK Polyetheretherketone is provided under the trade name SustaPEEK MG (Medical Grade) PEEK manufactured by Rochling.

Figure 13:
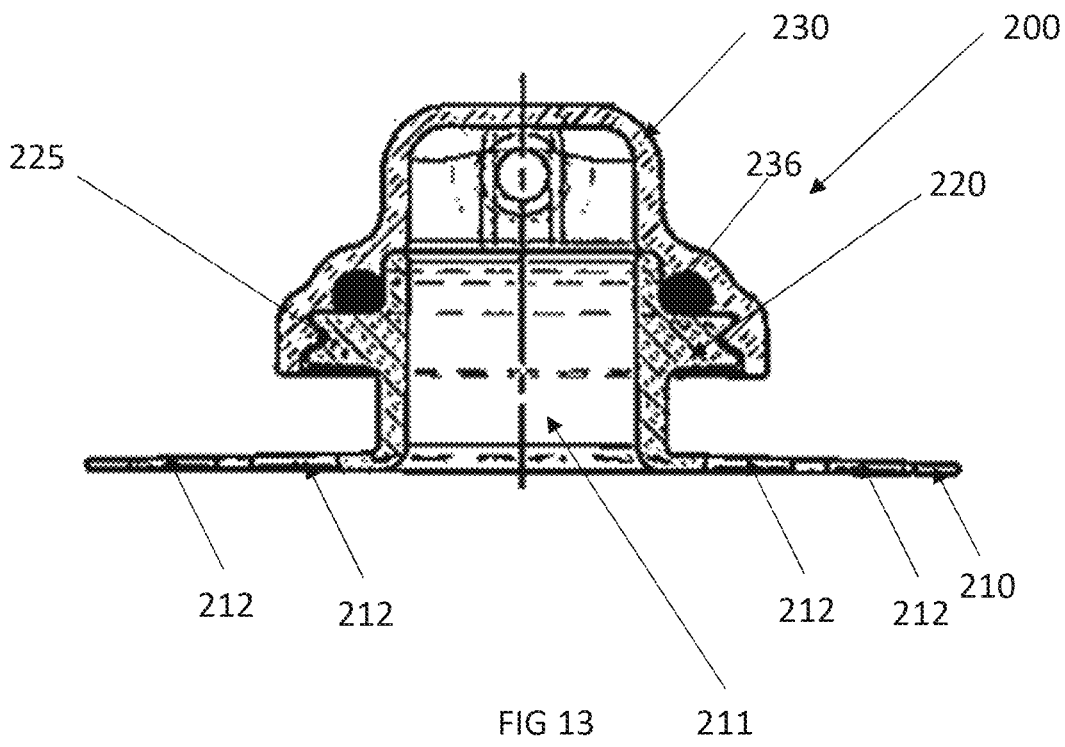
FIG. 13 shows yet another embodiment of the stoma implant assembly.
Figure 14:
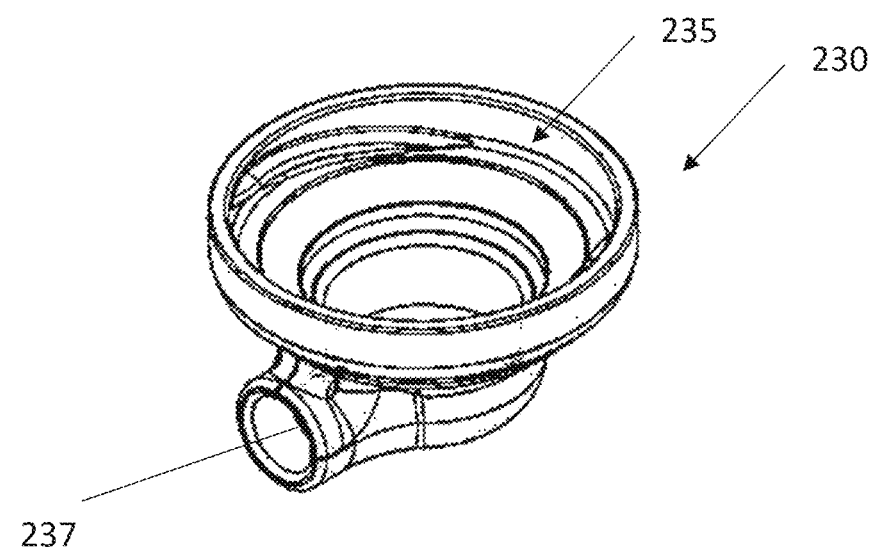
FIG. 14 shows an embodiment of the cover.

Shown in FIG. 13 is another embodiment similar to that of stoma implant assembly 200. For ease of description and brevity, the same numbering has been utilized. The main difference between the embodiment shown in FIG. 13 and that of FIGS. 11 and 12 is that the connecting portion of the outlet comprises a male threaded portion 225a at or adjacent a distal end thereof. In one embodiment, the outlet comprises the connecting portion at or adjacent the distal end. In one embodiment, the male threaded portion 225a may be provided on a flange or extension about the outlet 220. That is, the connecting portion comprises an extension or flange extending away from the outlet (in a substantially perpendicular direction). This extension or flange comprises the male thread thereon. The cover 230 suitably comprises a female threaded portion 235a which is complimentary to the male threaded portion 225a. In one embodiment, the female thread is located on an inner surface of the cover. This allows for the cover 230 to be easily secured to the outlet by simply twisting it thereon.

The cover 230 may suitably comprise a seal member that forms a seal with the outlet 220. A non-limiting example of this seal is a ring. In an embodiment, the seal is an O-ring 236. As the cover 230 is secured to the outlet 220, the seal member deforms between the outlet 220 and the cover 230. This allows for a seal to be formed therebetween. It will be appreciated that a substantially watertight seal is formed between the base, the outlet and the cover. In a preferred embodiment, a fluid tight seal is formed between the base, the outlet and the cover.

The cover 230 may further comprise a stoma bag connection portion which allows for bodily fluids to be connected. The stoma bag connection portion 237 is adapted to connect and seal with a stoma bag. In one embodiment, the cover 230 may be formed with the stoma bag. In one embodiment, the stoma bag connection portion comprises or is a one-way valve such that bodily fluid is only allowed to flow one way (out of the body and into the stoma bag). In one embodiment, the stoma bag connection portion comprises a check valve. Non-limiting examples of a non-return valve is a diaphragm check valve, a ball check valve, a swing check valve, a butterfly check valve and a top and tilting-disk check valve. However, the person skilled in the art will appreciate that any non-return valves may be utilized.

In one embodiment, the cover does not comprise the stoma bag connection portion. As previously mentioned, the subject may wish to partake in activities in which a stoma bag may be an inconvenience. In these situations, a cover may be utilized to close off the stoma. This cover suitably comprises the second connecting portion that is reciprocal to the connecting portion 125. However, the second connecting portion is closed and, in use, does not expose the stoma to the external environment. Preferably, the cover forms a watertight seal with the outlet.

In one embodiment, the cover 230 is formed of a material that is biocompatible with the human body. In one embodiment, the cover 230 is formed of titanium. In one embodiment, the material is suitably a polymer. In an embodiment, the material is a semi-crystalline thermoplastic. In embodiments, the material is a polyetheretherketone. In a preferred embodiment, the material is PEEK Polyetheretherketone. One source of PEEK Polyetheretherketone is provided under the trade name SustaPEEK MG (Medical Grade) PEEK manufactured by Rochling.

In one embodiment, the invention resides in the cover. The cover is adapted to secure to the outlet. The cover is suitably connectable to a stoma bag, or is formed with a stoma bag. In this regard, a consumer may purchase a cover and/or stoma bag comprising the cover once the stoma implant assembly has been installed.

In use, the stoma implant assembly may be fitted in a subject by aligning the aperture of the base under the skin with an incision in the abdomen of the subject. In this regard, the aperture is adapted to engage an outlet. The outlet is then secured with the base through the incision in the abdomen. The outlet comprises the distal end having a connecting portion adapted to releasably secure a second connecting portion. A stoma is suitably located through the bore.

There may also be a further step of locating the second connecting portion of a stoma bag or cap over the connecting portion.

There may also be further step of engaging the clip over the second connecting portion of the stoma bag or cap and the connecting portion.

There may also be another step of disengaging the clip over the stoma bag or cap. In this regard, there may be a further step of placing another stoma bag of cap over the connecting portion and locating the clip thereover to secure thereto.

The above description of various embodiments of the present invention is provided for purposes of description to one of ordinary skill in the related art. It is not intended to be exhaustive or to limit the invention to a single disclosed embodiment. As mentioned above, numerous alternatives and variations to the present invention will be apparent to those skilled in the art of the above teaching. Accordingly, while some alternative embodiments have been discussed specifically, other embodiments will be apparent or relatively easily developed by those of ordinary skill in the art. Accordingly, this invention is intended to embrace all alternatives, modifications and variations of the present invention that have been discussed herein, and other embodiments that fall within the spirit and scope of the above described invention

The invention claimed is:

1. A stoma implant assembly comprising:

an outlet comprising a distal end having a connection portion adapted to releasably secure to a second connection portion;

a base having an aperture adapted to engage the outlet, wherein the base is adapted to engage a body of a subject, and wherein the outlet comprises a bore therethrough; and a cover comprising the second connecting portion, wherein the cover comprises a stoma bag connection portion, wherein the stoma bag connection portion comprises a check valve.

2. The stoma implant assembly of claim 1, wherein the connecting portion comprises a male thread.

3. The stoma implant assembly of claim 1, wherein the second connecting portion comprises a female thread.

4. The stoma implant assembly of claim 1, wherein the base comprises one or more engagement apertures.

5. The stoma implant assembly of claim 4, wherein the one or more engagement apertures located concentrically around the aperture.

6. The stoma implant assembly of claim 1, wherein the cover comprises a seal member adapted to form a seal between the cover and the outlet.

7. The stoma implant assembly of claim 1, wherein the cover is adapted to connect to, or is formed with, a stoma bag.

8. The stoma implant assembly of claim 6, wherein the check valve is a ball check valve or a diaphragm check valve.

9. The stoma implant assembly of claim 1, wherein the base, outlet and/or cover is formed of a biocompatible material.

10. The stoma implant assembly of claim 9, wherein the biocompatible material is PEEK.

11. The stoma implant assembly of claim 1, for use in colostomy.

12. The stoma implant assembly of claim 1, when used in colostomy.

13. A method for fitting a stoma implant assembly in a subject, the method including the steps of:

aligning an aperture of a base under the skin with an incision in the abdomen of the subject, wherein the aperture is adapted to engage an outlet;

securing the outlet with the base through the incision, wherein the outlet comprises a distal end having a connecting portion adapted to releasably secure a second connecting portion, and wherein the outlet comprises a bore therethrough, and securing a cover comprising the second connection portion, wherein the cover comprises a stoma bag connection portion, wherein the stoma bag connection portion comprises a check valve to thereby fit the stoma implant assembly in a subject.

14. The stoma implant assembly of claim 1, wherein the outlet and base are integrally formed.

* * * * *